(12) United States Patent
Clevenger

(10) Patent No.: US 8,703,715 B2
(45) Date of Patent: *Apr. 22, 2014

(54) METHODS FOR INHIBITING GROWTH OF PROLACTIN-RESPONSIVE CANCER CELLS WITH CYCLOSPORINE A OR OTHER CYCLOPHILIN INHIBITORS

(71) Applicant: The Trustees of the University of Pennsylvania, Philadelphia, PA (US)

(72) Inventor: Charles V. Clevenger, Elmhurst, IL (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/746,843

(22) Filed: Jan. 22, 2013

(65) Prior Publication Data

US 2013/0157962 A1 Jun. 20, 2013

Related U.S. Application Data

(63) Continuation of application No. 12/711,580, filed on Feb. 24, 2010, now Pat. No. 8,357,660, which is a continuation of application No. 11/258,786, filed on Oct. 26, 2005, now Pat. No. 7,691,812.

(60) Provisional application No. 60/625,701, filed on Nov. 4, 2004.

(51) Int. Cl.
*A61K 38/13* (2006.01)

(52) U.S. Cl.
USPC .......................... 514/19.4; 514/19.5; 514/19.9

(58) Field of Classification Search
None
See application file for complete search history.

(56) References Cited

U.S. PATENT DOCUMENTS

| 5,051,402 | A | 9/1991 | Kurihara et al. | 514/20.5 |
| 5,994,299 | A | 11/1999 | Barriere et al. | 514/3.8 |
| 6,395,770 | B1 * | 5/2002 | Broder et al. | 514/449 |
| 7,691,812 | B2 * | 4/2010 | Clevenger | 424/278.1 |
| 8,357,660 | B2 * | 1/2013 | Clevenger | 514/19.5 |
| 2004/0171532 | A1 | 9/2004 | Broder et al. | 424/456 |
| 2006/0147914 | A1 * | 7/2006 | Worley | 435/6 |

OTHER PUBLICATIONS

Bernard et al. Effects of Cyclosporine A on Ia Antigen Expression in N-Nitroso-N-methylurea-induced Rat Mammary Tumors. Cancer Research. Jun. 1, 1990, vol. 50, pp. 3301-3305.*
Bernard et al. Antagonism of Prolactin Binding by Cyclosporine A on MCF Breast Tumor Cell Line. Anticancer Research. 1991, vol. 11, pp. 2147-2152.*
Bazars, F.J. "Haemopoietic Receptors and Helical Cytokines" Immunology Today 1990 11(10):350-354.
Bernard et al. "Effects of Cyclosporine A on Ia Antigen Expression in N-Nitroso-N-methylurea-induced Rat Mammary Tumors" Cancer Research 1990 50:3301-3305.
Bernard et al. "Antagonism of Prolactin Binding by Cyclosporine A on MCF Breast Tumor Cell Line" Anticancer Research 1991 11:2147-2152.
Bram et al. "Calcium Signalling in T Cells Stimulated by a Cyclophilin B-binding Protein" Nature 1994 371:355-358.
Bram et al. "Identification of the Immunophilins Capable of Mediating Inhibition of Signal Transduction by Cyclosporin A FK506:Roles of Calcineurin Binding and Cellular Location" Molecular and Cellular Biology 1993 13(8):4760-4769.
Clevenger et al. "Prolactin Receptor Signal Transduction in Cells of the Immune System" Journal of Endocrinology 1998 157:187-197.
Clevenger et al. "Expression of Prolactin and Prolactin Receptor in Human Breast Carcinoma" American Journal of Pathology 1995 146(3):695-705.
Clevenger et al. "Regulation of Interleukin 2-Driven T-lymphocyte Proliferation by Prolactin" Proceedings of the National Academy of Sciences USA 1990 87:6460-6464.
Clevenger et al. "Prolactin as an Autocrine/Paracrine Factor in Breast Tissue" Journal of Mammary Gland Biology and Neoplasia 1997 2(1):59-68.
Dardenne et al. "Prolactin Receptor Expression in Human Hematopoietic Tissues Analyzed by Flow Cytofluorometry" Endocrinology 1994 134(5):2108-2114.
DiMattia et al. "A Human B-Lymphoblastoid Cell Line Produces Prolactin" Endocrinology 1998 122(6):2508-2517.
Favy et al. "Cyclosporine a Inhibition of Prolactin-Dependent Up-Regulation of BRCA1 Protein Expression in Human Breast Cell Lines" Anticancer Research 2000 20:1703-1704.
Fields et al. "Detection of Prolactin Messenger RNA in Mammary and Other Normal and Neoplastic Tissues by Polymerase Chain Reaction" Laboratory Investigation 1993 68(3):354-360.
Friedman et al. "Two Cytoplasmic Candidates for Immunophilin Action are Revealed by Affinity for a New Cyclophilin: One in the Presence and One in the Absence of CsA" Cell 1991 66:799-806.
Gala, R.R. "Prolactin and Growth Hormone in the Regulation of the Immune System (43286B)" Proceedings of the Society for Experimental Biology and Medicine 1991 198:513-527.
Gellersen et al. "Nonpituitary Human Prolactin Gene Transcription is Independent of Pit-1 and Differentially Controlled in Lymphocytes and in Endometrial Stroma" Molecular Endocrinology 1994 8:356-373.
Ginsburg et al. "Prolactin Synthesis and Secretion by Human Breast Cancer Cells" Cancer Research 1995 55:2591-2595.
Kelly et al. "The Growth Hormone/Prolactin Receptor Family" Recent Progress in Hormone Research 1993 48:123-164.
Kooijman et al. "Prolactin, Growth Hormone, and Insulin-like Growth Factor-1 in the Immune System" Advances in Immunology 1996 63:377-454.
Krönke et al. "Cyclosporin a Inhibits T-cell Growth Factor Gene Expression at the Level of mRNA Transcription" Proceedings of the National Academy of Sciences 1984 81:5214-5218.
Lim et al. "Cyclosporin A Enhances the Apoptotic Effects of N-(4-hydroxyphenyl) Retinamide in Breast Cancer Cells" International Journal of Cancer 2002 101:243-247.

(Continued)

*Primary Examiner* — Jeffrey E Russel
(74) *Attorney, Agent, or Firm* — Licata & Tyrrell P.C.

(57) ABSTRACT

Methods are provided for inhibiting growth of prolactin-responsive cancer cells and treating prolactin-responsive malignancies via administration of an agent such as cyclosporine A which directly inhibits an enzymatic activity of a cyclophilin.

6 Claims, No Drawings

(56) References Cited

OTHER PUBLICATIONS

Liu et al. "Calcineurin is a Common Target of Cyclophilin-Cyclosporin A and FKBP-FK506 Complexes" Cell 1991 66:807-815.

Malarkey et al. "Physiological Concentrations of Prolactin Can Promote the Growth of Human Breast Tumor Cells in Culture" The Journal of Clinical Endocrinology & Metabolism 1983 53(4):673-677.

Malingre et al. "The Effect of Different Doses of Cyclosporin A on the Systemic Exposure of Orally Administered Paclitaxel" Anti-Cancer Drugs 2001 12:351-358.

Manni et al. "Promotion by Prolactin of the Growth of Human Breast Neoplasms Cultured in Vitro in the Soft Agar Clonogenic Assay" Cancer Research 1986 46:1669-1672.

McCaffrey et al. "NF-$AT_p$, a T Lymphocyte DNA-binding Protein That is a Target for Calcineurin and Immunosuppressive Drugs" The Journal of Biological Chemistry 1993 268(5):3747-3752.

Mershon et al. "Prolactin Is a Local Growth Factor in Rat Mammary Tumors" Endocrinology 1995 136(8):3619-3623.

Mertani et al. "Cellular Expression of Growth Hormones and Prolactin Receptors in Human Breast Disorders" International Journal of Cancer (Predictive Oncology) 1998 79:202-211.

Montgomery et al. "Concanavalin A-Stimulated Murine Splenocytes Produce a Factor with Prolactin-Like Bioactivity and Immunoreactivity" Biochemical and Biophysical Research Communications 1987 145(2):692-698.

Ormandy et al. "Coexpression and Cross-Regulation of the Prolactin Receptor and Sex Steroid Hormone Receptors in Breast Cancer" The Journal of Clinical Endocrinology & Metabolism 1997 82(11):3692-3699.

Pellegrini et al. "Expression of Prolactin and Its Receptor in Human Lymphoid Cells" Molecular Endocrinology 1992 6:1023-1031.

Prystowsky et al. "Prolactin as a Second Messenger for Interleukin 2" Immunomethods 1994 5:49-55.

Rycyzyn et al. "Role of Cyclophilin B in Prolactin Signal Transduction and Nuclear Retrotranslocation" Molecular Endocrinology 2000 14 (8):1175-1186.

Rycyzyn et al. "The Intranuclear Prolactin/Cyclophilin B Complex as a Transcriptional Inducer" Proceedings of the National Academy of Sciences USA 2002 99(10):6790-6795.

Shiu et al. "Biological Actions of Prolactin in Human Breast Cancer" Recent Progress in Hormone Research 1987 43:277-289.

Syed et al. "A Novel and Functional Interaction Between Cyclophilin A and Prolactin Receptor" Endocrine 2003 20:83-89.

Weigent, D.A. "Immunoregulatory Properties of Growth Hormone and Prolactin" Pharmacology Therapy 1996 69(3):237-257.

Welsch et al. "Prolactin and Murine Mammary Tumorigenesis: A Review" Cancer Research 1977 37:951-963.

Welsch et al. "Host Factors Affecting the Growth of Carcinogen-induced Rat Mammary Carcinomas: A Review and Tribute to Charles Brenton Huggins" Cancer Research 1985 45:3415-3443.

Yu-Lee, Ly. "Molecular Actions of Prolactin in the Immune System (44111)" Proceedings of the Society for Experimental Biology and Medicine 215:35-52 (1997).

Office Communication dated May 18, 2006 from U.S. Appl. No. 11/258,786, filed Oct. 26, 2005.

Office Communication dated Dec. 13, 2006 from U.S. Appl. No. 11/258,786, filed Oct. 26, 2005.

Office Communication dated Jun. 7, 2007 from U.S. Appl. No. 11/258,786, filed Oct. 26, 2005.

Office Communication dated Oct. 22, 2007 from U.S. Appl. No. 11/258,786, filed Oct. 26, 2005.

Office Communication dated Mar. 31, 2008 from U.S. Appl. No. 11/258,786, filed Oct. 26, 2005.

Office Communication dated Jan. 13, 2009 from U.S. Appl. No. 11/258,786, filed Oct. 26, 2005.

Office Communication dated Apr. 21, 2009 from U.S. Appl. No. 11/258,786, filed Oct. 26, 2005.

Office Communication dated Dec. 13, 2011 from U.S. Appl. No. 12/711,580, filed Feb. 24, 2010.

Office Communication dated May 31, 2012 from U.S. Appl. No. 12/711,580, filed Feb. 24, 2010.

* cited by examiner

METHODS FOR INHIBITING GROWTH OF PROLACTIN-RESPONSIVE CANCER CELLS WITH CYCLOSPORINE A OR OTHER CYCLOPHILIN INHIBITORS

INTRODUCTION

This application is a continuation of U.S. Ser. No. 12/711,580 filed Feb. 24, 2010, which is a continuation of U.S. Ser. No. 11/258,786 filed Oct. 26, 2005, now issued as 7,691,812, which claims the benefit of priority from U.S. Provisional Application Ser. No. 60/625,701, filed Nov. 4, 2004, which are herein incorporated by reference in their entireties.

FIELD OF THE INVENTION

Methods are provided for inhibiting growth of prolactin-responsive cancers such as breast cancer and prostate cancer via administration of low doses of a cyclosporine A and/or another agent which directly inhibits an enzymatic activity of cyclophilins. Compositions comprising a cyclosporine A and/or another agent which directly inhibits an enzymatic activity of cyclophilins are expected to be useful in treatment of prolactin-responsive malignancies.

BACKGROUND OF THE INVENTION

Cyclosporine A, the active principal in NEORAL and SANDIMMUNE, is a cyclic polypeptide immunosuppressant agent. NEORAL and SANDIMMUNE are indicated for use in kidney, liver and heart transplantation, rheumatoid arthritis, and adult, non-immunocompromised patients with severe psoriasis. However, use of NEORAL and SANDIMMUNE has been linked to an increased susceptibility to infection and development of neoplasia, and more specifically with respect to SANDIMMUNE, development of lymphoma.

Cyclophilin proteins have been identified as the binding partners for the immunosuppressive agent cyclosporine. Cyclosporine A interacts with cyclophilins with high affinity, inhibiting their cis-trans peptidyl prolyl isomerase activity and the action of the phosphatase calcineurin, necessary for NF/AT-transactivated expression of IL-2 (Kronke et al. Proc. Natl Acad. Sci. USA 1984 81:5214; Liu et al. Cell 1991 55:807; Friedman, J. and Weissman, I. Cell 1991 66:799; McCaffrey et al. J. Biol. Chem. 1993 268:3747; Bram, R. J. and Crabtree, G. R. Nature 1994 371:355; Bram et al. Mol. Cell Biol. 1993 13:4760).

Cyclophilin B interacts specifically with somatolactogenic hormones, prolactin and growth hormone, as a chaperone mediating the transport, maturation and/or function of these proteins (Rycyzyn et al. Mol. End. 2000 14:1175-1186; Rycyzyn and Clevenger Proc. Natl Acad. Sci. USA 2002 99:6790-6795). These hormones are necessary for the full growth and maturation of vertebrate species.

Prolactin was originally identified as a neuroendocrine hormone of pituitary origin. Prolactin expression has also been detected in the decidua, breast and T-lymphocytes (Clevenger, C.V. and Plank, T. L. J. Mammary Gland Biol. Neoplasia 1997 2:59-68; Mershon et al. Endocrinology 1995 136:3619-3623; DiMattia et al. Endocrinology 1986 122: 2508-2517; Ginsburg, E. and Vonderhaar, B. K. Cancer Res. 1995 55:2591-2595; Gellersen et al. Mol. Endocrinol. 1994 8:356-373; Clevenger et al. Proc. Natl Acad. Sci. USA 1990 87: 6460-6464; Montogomery et al. Biochem. Biophys. Res. Commun. 1987 145:692-698). A primary function of this hormone lies within the breast. However, functional pleiotropism of this peptide with regard to reproduction, osmoregulation and behavior has also been recognized (Nicoll, C. S. Handbook of Physiology; Section 7: Endocrinology, pp. 253-292, Washington, D.C.: American Physiology Society. 1974). Several lines of evidence have also indicated an immunoregulatory role for this peptide (Clevenger et al. Journal of Endocrinology 1998 157:187-197; Weigent, D. A. Pharmacol. Ther. 1996 69:237-257). Structural analysis of prolactin has revealed it to be related to members of the cytokine/hematopoietin family which also includes growth hormone, erythropoietin, granulocyte-macrophage colony stimulating factor and interleukins 2-7 (Bazan, J. F. Immunol. Today 1990 11:350-354). The pleiotropic actions of prolactin are mediated through its receptor (PRLr), a member of the superfamily of type I cytokine receptors. PRLr is present on numerous tissues including mammary epithelia, T and B lymphocytes and macrophages (Dardenne et al. Endocrinology 1994 134: 2108-2114; Pellegrini et al. Mol, Endocrinol. 1992 6:1023-1031). Acting through its receptor, prolactin signaling stimulates cell proliferation, survival and cellular differentiation in a tissue- and microenvironment-dependent manner. In the mammary and immune systems, prolactin is believed to act at the endocrine, paracrine, and autocrine levels in regulating T-lymphocyte proliferation and survival (Gala, R. R. PSEBM 1991 198:513-527; Yu-Lee, L. Y. Proceedings of the Society for Experimental Biology and Medicine 1997 215:35-52; Kooijman et al. Adv. Immunol. 1996 63:377-454; Prystowski, M. B. and Clevenger, C. V. Immunomethods 1994 5:49-55) and the terminal maturation of mammary tissues (Kelly et al. Rec. Prog. Horm. Res. 1993 48:123-164; Shiu et al. Rec. Prog. Horm. res. 1987 43:277-289). Prolactin is also believed to act as both an endocrine and autocrine/paracrine progression factor for mammary carcinoma in both rodents and humans (Welsch, C. W. Cancer Res. 1985 45:3415-3443; Welsch, C. W. and Nagasawa, H. Cancer Res. 1977 37:951-963; Manni et al. Cancer Res. 1986 37:951-963; Malarkey et al. J. Clin. Endocrinol. Metab. 1983 56:673-677; Clevenger et al. Am. J. Pathol. 1995 146:1-11; Fields et al. Lab. Invest. 1993 68:354-360; Ormandy et al. J. Clin. Endocrinol. Metab. 1997 82:3692-3699; and Mertani et al. Int. J. Cancer 1998 79:202-22).

Cyclophilin A has also been demonstrated to interact directly with PRLr in in vitro binding assays and regulate prolactin signaling (Syed et al. Endocrine 2003 20(½)83-89). This direct interaction occurred in the presence and absence of cyclosporine (Syed et al. Endocrine 2003 20(½):83-89).

SUMMARY OF THE INVENTION

An object of the present invention is to provide methods for inhibiting growth of prolactin-responsive cancer cells which comprises administering to the cells cyclosporine A or another agent which directly inhibits an enzymatic activity of cyclophilins.

Another object of the present invention is to provide a method for treating a prolactin-responsive malignancy in a subject which comprises administering to the subject cyclosporine A or another agent which directly inhibits an enzymatic activity of cyclophilins.

DETAILED DESCRIPTION OF THE INVENTION

The present invention provides methods for inhibiting growth of prolactin-responsive cancer cells and methods for treating prolactin-responsive malignancies. Examples of prolactin-responsive malignancies include, but are not limited to, cancers occurring in the breast and prostate. In the methods of the present invention, growth of the cancer cells is inhibited by administering to the cells an agent which directly inhibits enzymatic activity of cyclophilins. In a preferred embodiment, the agent administered to the cells inhibits the activity of cyclophilin A. An exemplary agent is a cyclosporine such as cyclosporine A. Preferably, the cells are administered a low dose of cyclosporine A.

It has now been found that media concentrations of as little as 20 ng (nanograms)/ml of cyclosporine A have profound effects on survival of breast cancer cells. In these experiments, currently available pharmacologic formulations of cyclosporine include NEORAL and SANDIMMUNE were tested on a variety of normal and malignant breast cell lines under a variety of culture condition. Both formulations of cyclosporine were found to be effective at low doses at inhibiting growth of breast cancer cells.

Based upon these experiments, it is expected that cyclosporine A administration will also be effective in inhibiting growth of other prolactin-responsive cancers including, but in no way limited to prostate cancer.

Further, since the activity of cyclosporine A in inhibiting growth of these cancer cells is believed to be related to its direct inhibition of the enzymatic activity of cyclophilins, and more particularly cyclophilin A, from the experiments described herein it is expected that other agents which directly inhibit the enzymatic activity of cyclophilins can also be used in the inhibition of growth and treatment of prolactin-responsive cancers.

Cyclosporine A is an FDA approved drug for use as an immunosuppressive agent. Peak serum concentrations of cyclosporine A for approved indications can reach 2-8 µg/ml in human patients. Based upon cell culture experiments described herein, it is expected that a significantly lessened dosage as compared to that used in immunosuppressive therapies can be used for treatment of breast cancer and other prolactin responsive cancers such as prostate cancer. However, if needed, up to 9 mg/kg/day of NEORAL has been tolerated. The cyclosporine containing agent can be administered either intravenously or orally in accordance with well-established dosing regimes for NEORAL or SANDIMMUNE.

What is claimed is:

1. A method for treating a prolactin-responsive malignancy in a subject comprising administering to the subject an agent which directly inhibits an enzymatic activity of cyclophilins, and wherein said agent that inhibits cyclophilins is administered by itself and further wherein said agent is administered at a significantly lessened dosage as compared to that used in immunosuppressive therapies.

2. The method of claim 1 wherein the cyclophilin is cyclophilin A.

3. The method of claim 1 wherein the agent is a cyclosporine.

4. The method of claim 1 wherein the agent is cyclosporine A.

5. The method of claim 1 wherein the prolactin-responsive malignancy is breast cancer.

6. The method of claim 1 wherein the prolactin-responsive malignancy is prostate cancer.

* * * * *